United States Patent [19]

Porter

[11] 4,358,960
[45] * Nov. 16, 1982

[54] DIFFERENTIAL FIBER OPTIC PROXIMITY SENSOR

[75] Inventor: John H. Porter, Colchester Point, Vt.

[73] Assignee: Ladd Research Industries, Inc., Burlington, Vt.

[*] Notice: The portion of the term of this patent subsequent to Jul. 1, 1997, has been disclaimed.

[21] Appl. No.: 163,157

[22] Filed: Jun. 26, 1980
(Under 37 CFR 1.47)

Related U.S. Application Data

[63] Continuation-in-part of Ser. No. 36,246, May 4, 1979, Pat. No. 4,210,029.

[51] Int. Cl.³ .................... G01B 11/14; G01L 9/00
[52] U.S. Cl. ............................... 73/705; 73/723; 250/227; 250/559; 356/375; 356/381
[58] Field of Search .................... 73/705, 723, 313; 356/375, 381, 371, 376; 250/227, 559, 560

[56] References Cited

U.S. PATENT DOCUMENTS

| | | | |
|---|---|---|---|
| 3,327,584 | 6/1967 | Kissinger | 356/375 |
| 3,503,116 | 3/1970 | Strack | 73/705 |
| 3,580,082 | 5/1971 | Strack | 73/705 |
| 3,686,958 | 8/1972 | Porter et al. | 73/705 |
| 3,778,157 | 12/1973 | Brelot et al. | 250/227 |
| 3,789,667 | 2/1974 | Porter et al. | 73/705 |
| 4,210,029 | 7/1980 | Porter | 73/705 |

Primary Examiner—Donald O. Woodiel
Attorney, Agent, or Firm—W. R. Hulbert

[57] ABSTRACT

Proximity sensor for determining the distance between a reflective surface and the sensor utilizes two output light guides positioned with the receiving end of one guide closer to the reflective surface than that of the other. When the surface is close to the guide ends a relatively greater intensity of light will be reflected to the second guide; when the surface is further away a relatively greater intensity of light will be reflected to the first guide. At a predetermined intermediate null position the reflected light intensities will be equal. The device has uses, inter alia, in accurately positioning objects without wear-producing contact, e.g. in numerically controlled machine tool operations; thickness sensing or thickness controlling using single or dual sensors; force sensing; liquid level indication; meter relay actuation; rotational limitation, and the like.

27 Claims, 18 Drawing Figures

DIFFERENTIAL FIBER OPTIC PROXIMITY SENSOR

BACKGROUND OF THE INVENTION

This is a continuation-in-part of my co-pending, allowed application, Ser. No. 36,246, filed May 4, 1979, entitled, "Differential Fiber Optic Differential Pressure Sensor," now U.S. Pat. No. 4,210,029 the text of which is hereby incorporated by reference herein.

This invention relates to proximity sensing by comparing the intensities of light reflected by a reflective body in which the light is directed at the body and the reflective light received from the body through light guides, such as bundles of light conducting fibers.

In my said co-pending application, a device is shown for measuring intra-cranial pressure, and the like, employing a sensor comprising a bundle of light guides enclosed in a housing one wall of which is flexible and carries a reflective surface. The internal ends of the guides face the reflective surface. One guide transmits light and directs it at the surface. The others receive the reflected light. The ends are so arranged that the light path from the input guide to the reflective surface and back to one of the receiving guides is longer than the corresponding path to the other receiving guide. Thus, if the reflective surface is flexed toward or away from the ends of the guides, the intensity of reflected light received by each receiving guide differs with differing characteristics and a comparison thereof can therefore be related to the motion of the flexible wall permitting sensing thereof together with the use of a servo to restore the wall to its original position by varying the pressure within the housing.

I have found that the above described principle may be extended to proximity sensing more generally, making possible substantial improvements in and simplification of known devices employing fiber optics for this purpose. For example, in U.S. Pat. No. 3,778,157, there are disclosed several embodiments of apparatus for producing signals varying as a function of the distance of a surface to a reference face employing fiber optics for directing light onto a reflective surface and receiving reflected light therefrom. In U.S. Pat. No. 3,327,584, there is shown one embodiment (FIG. 28) employing a pair of distinct fiber optic probes, each having input and output light guides, a light source and a light detector. One probe is placed closer to the reflective object than the other and complex electronic means are provided for comparing the intensity of reflected light reaching each output light guide. Even this device is essentially only a two guide system.

The typical two light guide (two path) sensor of the prior art attempts to measure distance using an absolute intensity range, which unfortunately, includes variable amounts of ambient and stray light. Since there is no mechanical null point (where electrical gain can be very high regardless of electrical system linearity), the two guide sensor has to maintain both amplifiers and photodetectors in the lower gain, linear region where small errors of measurement, unfortunately, cannot be detected. Also, electrical drift of the light source and the photodetector are included as errors of variable and unknown magnitudes. The use of filters on the two guide system helps exclude some of the ambient light but at a consequent source light loss that can interfere with measurements of objects with low light reflectivity. "Chopping" of the light source helps to minimize electrical drift effects but there is the problem of securing a photodetector that is not only linear but also "fast" enough to follow the pulse rate of the chopped light signal.

A principal object of the invention is to provide a new and improved proximity sensor employing fiber optics and the principle of measuring the relative intensities of reflected light wherein light from a point source is directed through a single light guide onto the reflective surface of a body whose relative distance from the sensor is to be measured, the reflected light being received simultaneously by and transmitted to appropriate detecting and measuring means through a pair of output light guides so arranged that the relative intensities of reflected light vary differentially with change of the relative distance aforesaid. The invention thus provides a three-guide rather than a two-guide system with inherent advantages as will appear hereinafter.

SUMMARY OF THE INVENTION

According to the invention, there is provided a proximity sensor for use in apparatus capable of translating the relative intensity of transmitted reflected light into signals indicative of the distance between the sensor and the reflective surface of a body which comprises means for directing light at the surface from a point source, a pair of output light guides arranged with their light receiving ends facing the surface to receive and transmit the reflected light, the light receiving end of one of the guides, when the sensor is in operative position, being closer to the reflective surface than the other, whereby the intensities of reflected light received and transmitted by the guides will be equal at a predetermined null position of the body with respect to the light receiving ends and will vary differentially as a function of change of distance between the guide ends and the body. In preferred embodiments, the means for directing light comprises an input light guide and all the light guides are bundled together in a housing; light detectors are provided to detect the intensities of reflected light transmitted by the output guides; means are provided for adjusting at least the light receiving end of one of the output guides toward and away from the reflective surface to establish the null point and this adjusting means may be arranged to move the entire housing or only the one of the output guides whose light receiving end is closer to the reflective surface; the device is adaptable for use as a thickness gauge, utilizing one or more sensor heads, as a force sensor, pressure sensor, liquid level indicator or meter-relay.

DETAILED DESCRIPTION OF PREFERRED EMBODIMENTS

Figure 1:
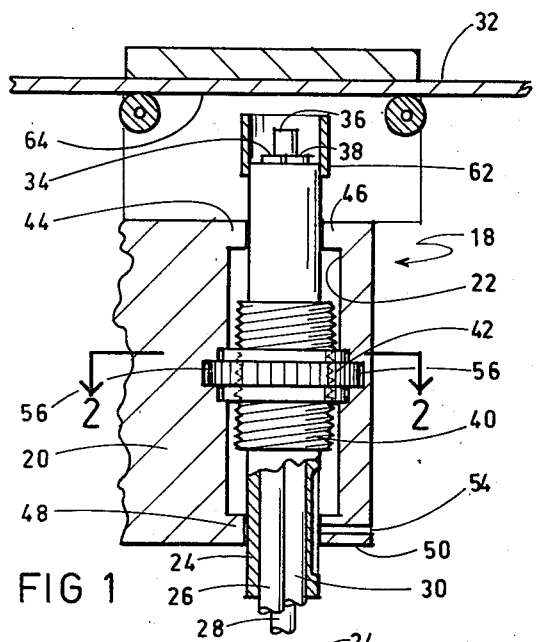
FIG. 1 is a vertical sectional view of a sensor embodying the invention.
Figure 2:
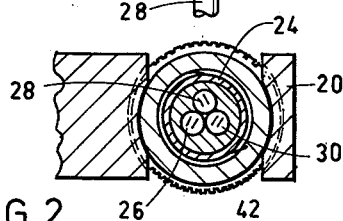
FIG. 2 is a section taken on line 2—2 of FIG. 1.

Referring first to FIGS. 1 and 2, one presently preferred embodiment of a sensor head 18 of the invention is illustrated in a thickness gauge application. The sensor unit comprises a cylindrical housing 24 containing a bundle of three fiber optic light guides 26, 28 and 30 of which guide 26 conducts light from a source (not shown) to illuminate the surface 64 of travelling sheet 32 while guides 28 and 30 receive light reflected from said sheet and transmit the same to light detectors (not shown). Systems for detecting the intensity of reflected light and initiating suitable responses to the relative intensities detected will be described below in connection with the embodiments of FIGS. 6 and 11.

In order to mount the housing 24 so that the inner ends 34, 36 and 38 of guides 26, 28 and 30, respectively, will face the sheet 32 and be adjustable toward and away from the same, the housing 24 is surrounded by an externally threaded cylindrical member 40 which firmly grips or is integral with the housing surface. Threaded on the member 40 is an internally threaded collar 42. The housing is non-rotatably mounted in opening 22 in bracket 20 in such manner as to be slidable longitudinally toward and away from sheet 32. Arms 44, 46 bear against the housing 24 at the upper end (as seen in FIG. 1) and arms 48, 50 bear against it at the other end. Housing 24 is provided with a longitudinal groove 52 in the vicinity of arm 50 to slidably receive pin 54 which permits longitudinal movement of the housing but prevents rotation thereof. The collar 42 is journaled in grooves 56 whereby its rotation will advance or retract the unit with respect to the sheet 32 which travels in front of the ends 34, 36 and 38, its path being established by rollers 58 and backing 60. The inner ends of the light guides are shielded from transient light by shade 62.

In the embodiments of FIGS. 1 and 2 the entire sensor head is adapted for adjustment toward and away from the target whose proximity is to be sensed and this adjustment can be done manually or could be suitably mechanized for automatic operation, as will be discussed below. Before doing so, however, reference should now be had to the diagrammatic representations of FIGS. 13 and 14 from which the theory of operation will become clear. Reference should also be had to co-pending application Ser. No. 36,246 incorporated herein by reference.

As already seen in connection with the description of the embodiment of FIGS. 1 and 2, the inner end 36 of light guide 28 is arranged closer to the target, in this case, the reflective surface 64 of sheet 32, than are the ends 34 and 38 of the other guides. The outer end of guide 26 faces a light source and transmits the light therefrom to shine on the reflective surface 64 and be reflected back to the adjacent inner ends 36 and 38 of the two other light guides. The light paths are diagrammatically illustrated in FIG. 13 and plotted on the graph of FIG. 14.

Although, unlike the embodiment of the co-pending application, the guides are bodily movable toward and away from the surface 64 instead of vice versa, for theoretical discussion it is simpler to explain the principle of operation on the basis that the target rather than the guides can move, since the principle depends upon relative movement rather than absolute movement. Hence, in FIGS. 13 and 14 the surface 64 is assumed to be movable to different distances from the ends of the guides.

On this assumption, measurements are taken from a base plane Z which is the plane of the ends 34 and 38. Z–Y represents the distance from plane Z to the plane Y of the end 36. Z–N represents the distance from Z to the surface 64 at one arbitrary adjustment of the relative distance between the ends and the surface 64 and Z–X represents the corresponding distance when surface 64 and guide ends are further away from each other.

Figure 14:
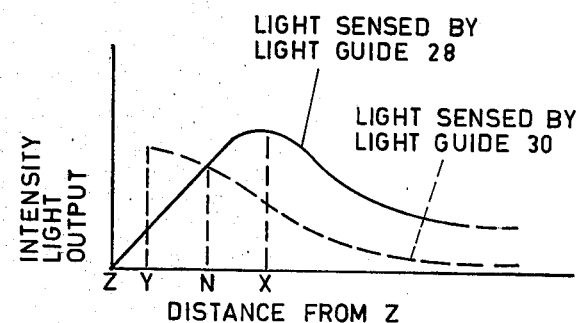
FIG. 14 is a graph showing the intensities of reflected light sensed by the output light guides at different distances from the reflective body as indicated in FIG. 13.

Now, considering FIG. 14, the abscissa represents the distances (Z–Y, Z–N and Z–X) of the reflective surface 64 from the faces 34 and 38 of the corresponding light guides 26 and 30. The ordinates depict the intensity of reflected light received by and transmitted to the external apparatus (discussed hereinafter) by the output guides 28 and 30 at different distances along the abscissa, yielding two curves which intersect at a null point N, the position when the two light outputs are equal. At the extreme inner position Y the reflective face 64 contacts or is so close to end 36 that essentially no light is reflected to guide 28, as indicated at Y on the graph. At this relative position, maximum light is reflected to output guide 30. As the distance between the surface 64 and the inner ends of the guides increases the intensity of light reflected to guide 30 decreases and that reflected to guide 28 increases, following the square law equation concerning illumination from a point source. At N the outputs of guides 28 and 30 are equal. At distances approaching Z–X guide 28 receives, and hence transmits, more light than does guide 30.

By coupling the outputs of guides 28 and 30 to a pair of photocells in suitable light detectors, connected in a differential configuration electrically, the relative intensity of the light outputs of the two fiber optics may be used to drive a servo mechanism which can vary or halt the processing of sheet 32, depending on the nature of the process being monitored. For example, in the FIG. 1 embodiment, if a travelling paper sheet is being monitored for thickness, any increase or decrease in its thickness will cause a corresponding change in the distance from Z to its surface 64. This, in turn, will produce altered differential light reflection which can be instantly detected with corresponding action by the servo to make suitable adjustments in the paper-making machine, or, indeed, to bring the operation to a halt so that corrective measures can be taken. By means of the adjusting collar 42 the position of the sensor with respect to the sheet 32 can be zero-adjusted so that correct sheet thickness is represented by the distance Z–N. Thus, if the sheet thickness increases, the distance from surface 64 to Z will decrease and light reflected to guide 30 will increase and reflected light transmitted by guide 28 will also increase to a maximum at distance Z–X and be suitably detected.

Figure 1A:
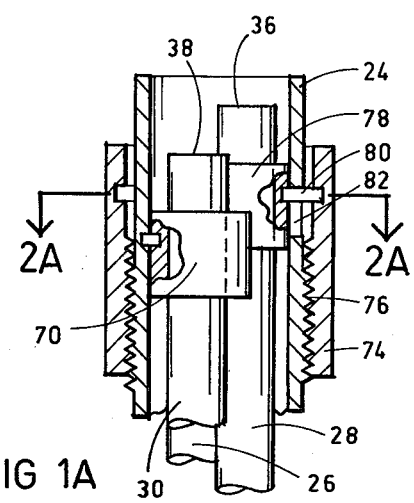
FIG. 1A is a similar view of an alternative embodiment.
Figure 2A:
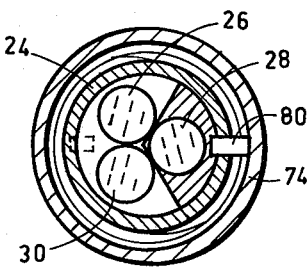
FIG. 2A is a section taken on line 2A—2A of FIG. 1A.

While for many purposes zero adjustment by bodily shifting the sensor toward and away from the target, as in the embodiment just discussed, is desirable, there may be cases where zero adjustment or calibration by adjusting the distance Z–Y is preferable. A suitable embodiment is shown in FIGS. 1A and 2A.

In this embodiment light fiber 28 is longitudinally shiftable with respect to the other two light fibers 26 and 30. In this instance housing 24A is slotted at 66 and 82. Guides 26 and 30 are clamped together by a holder 70 which is keyed to housing 24A by key 72 in slot 66 so as to prevent longitudinal or rotational movement thereof. Surrounding housing 24A is internally threaded sleeve 74 which is fixed by suitable means against longitudinal movement and which engages external threads 76. Sleeve 74 is joined to the holder 78 for fiber optic 28 by key 80 which can slide in slot 82 in the housing. In this fashion rotation of sleeve 74 will slide guide 28 in or out and will adjust the distance Z–Y (FIGS. 13 and 14) by which end 36 of guide 28 extends beyond the inner ends 34, 38 of the other two light guides 26, 30.

Referring back to FIG. 13, it will be seen that the change in the distance Z–Y will change the reflective characteristics such as to alter the curve of light sensed by guide 28 and correspondingly to change the distance Z–N thereby permitting nulling the sensor for any given use.

OTHER THICKNESS GAUGE EMBODIMENTS

Figure 5:
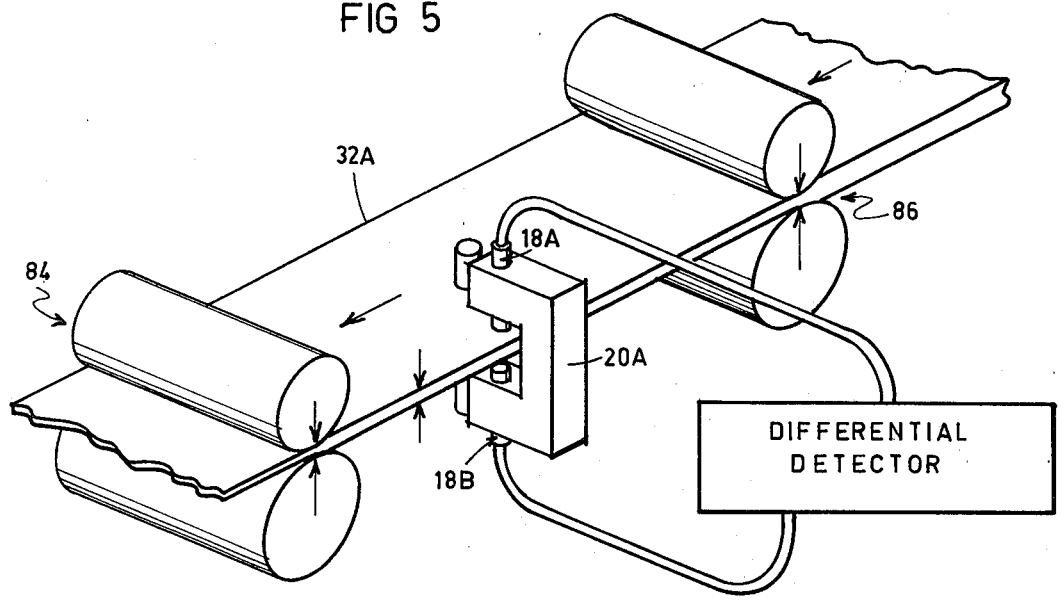
FIG. 5 is a somewhat diagrammatic perspective view of a two-sensor thickness gauge for continuously monitoring the thickness of a travelling sheet of material.
Figure 6:
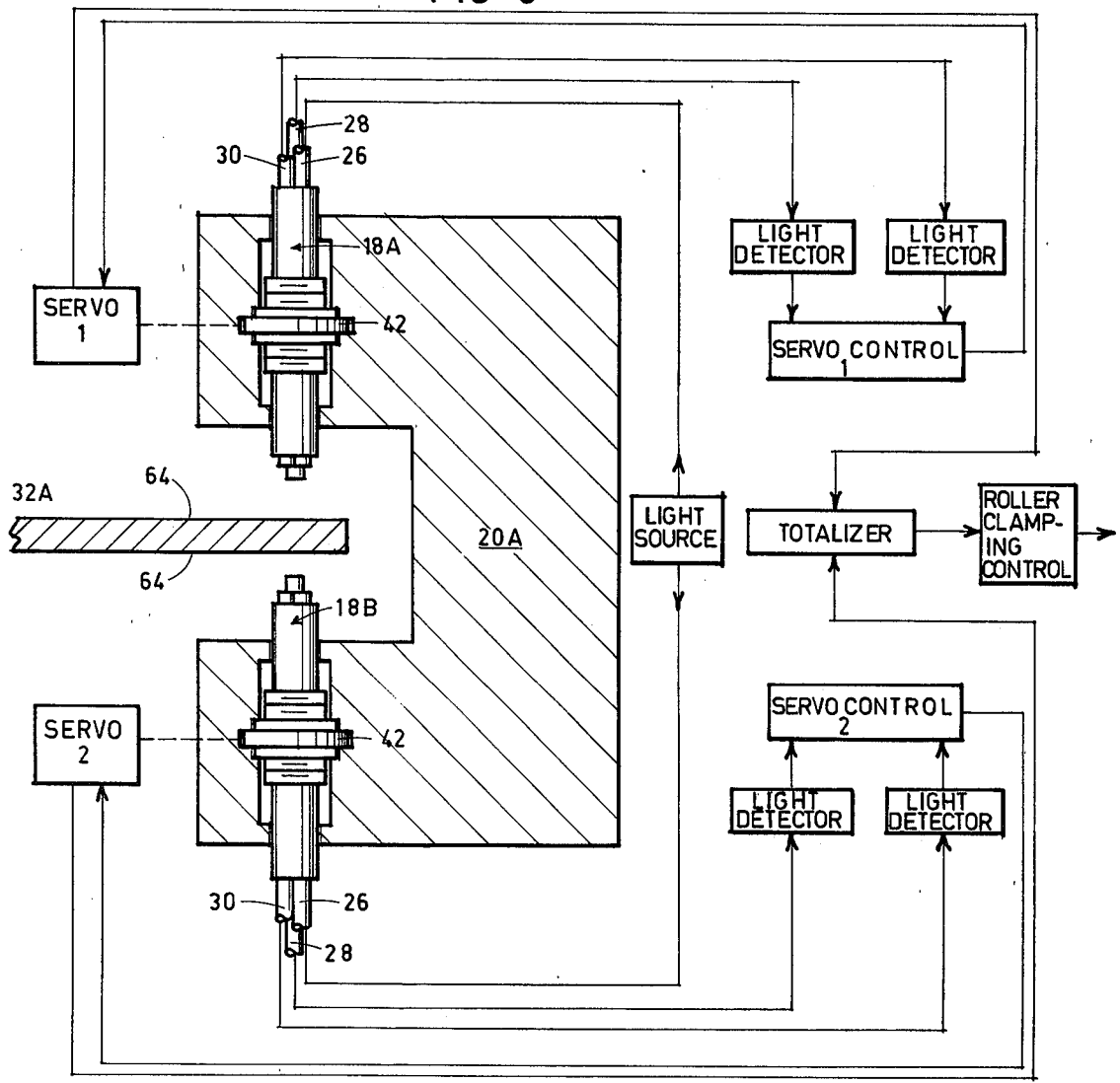
FIG. 6 is a cross-sectional view on an enlarged scale of a portion of the embodiment of FIG. 5 taken on line 6—6 of FIG. 5.

So far the invention has been described as applied specifically to thickness measurement where the thickness of a reflective sheet is sensed by a single proximity sensor placed opposite one of its flat surfaces. In FIGS. 5 and 6 the invention is shown as applied to a system for controlling sheet thickness by means of a pair of proximity sensors between which the sheet runs.

A pair of sensor heads 18A and 18B is mounted by bracket 20A with their light emitting and receiving (inner) ends on opposite sides of a metal sheet 32A being processed, in a rolling mill for example, having roller pairs 84 and 86. As best seen in FIG. 6, light is transmitted by light guides 26 of each sensor so as to be directed at opposite surfaces of the sheet 32A. Differential reflected light is transmitted back to pairs of light detectors and servo controls, as shown. Both sensor servos send position information to a "Totalizer" which calculates the thickness and compares it with that specified and sends roller clamping control correction signals to readjust the roll pairs 84, 86. The servos are coupled to the collars 42 of each head thereby enabling the totalizer to be nulled to the specified thickness by pre-adjustment of the collars.

In this embodiment the two heads are first nulled by rotating collars 42 so as to adjust the sensors toward and away from a sheet of known specified thickness having reflecting surfaces on both sides until they are spaced from each other by twice the distance Z–N (FIG. 13) plus the specified sheet thickness. In operation, if the sheet moves bodily toward one or the other sensing head, but without variation in sheet thickness, there will be no net change in the length of aggregate light paths to the input guides and the apparatus will, accordingly, ignore the change. However, if there is a variation in sheet thickness, the change will involve net change in the lengths of light paths and the apparatus will, accordingly, sense the change and initiate the desired action, as by changing the pressure of the clamping rolls 84, 86.

OTHER EMBODIMENTS

Figure 3:
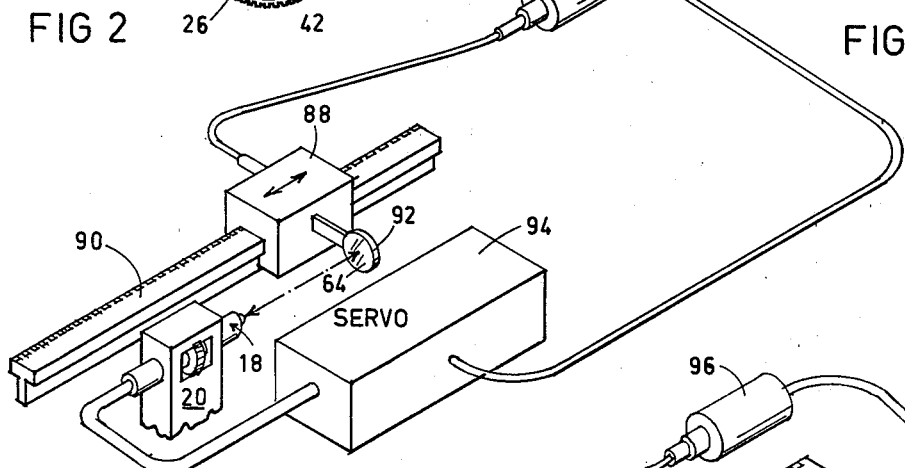
FIG. 3 is a somewhat diagrammatic perspective view of a system for controlling a reciprocating machine tool utilizing the novel proximity sensor.
Figure 4:
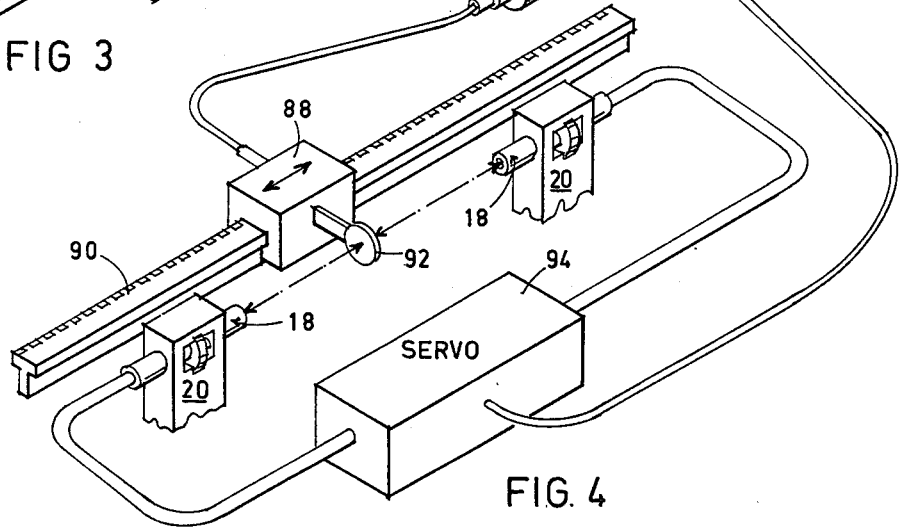
FIG. 4 is a view similar to FIG. 3 wherein a pair of the novel sensors is employed.

FIGS. 3 and 4 illustrate single and double sensor head embodiments, respectively, for controlling the operation of a reciprocating machine tool wherein an element, at each stroke, is to move to a specified limit position.

In FIG. 3, a body 88 reciprocates on rail 90 and is specified to halt at a given limiting position on each stroke. If sensor head 18 is mounted in bracket 20 so that the active ends of the light fibers face a reflector 92 having a reflecting surface 64 which travels with the body 88 and are located a predetermined distance from the specified position the reflector should occupy at the end of each stroke, the sensor will detect and report any variation within specified tolerances. The output guides transmit their sensed light to detectors in servo 94 which, through control 96, can make suitable adjustments in the machine to restore it to specifications.

FIG. 4 shows a similar system for sensing dual limits in a reciprocating machine tool employing a pair of sensing heads.

Figure 12:
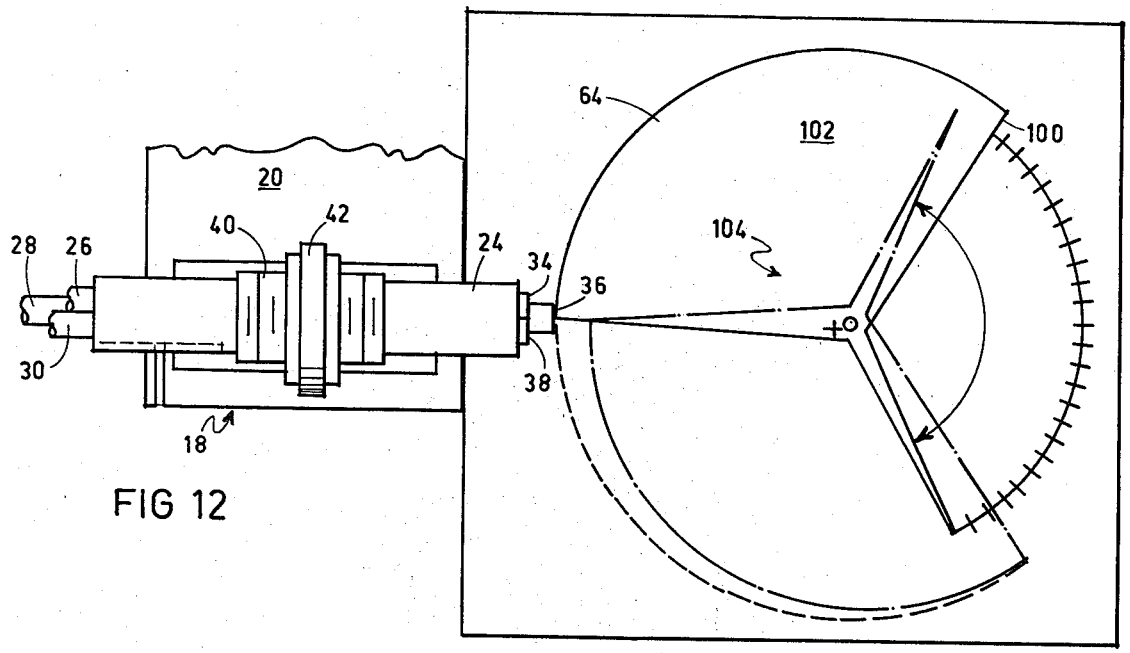
FIG. 12 is a plan view showing the sensor arranged as part of a meter relay.

The device may be used to actuate a meter relay as shown in FIG. 12. Cam-like reflective rim 100 of sector 102 attached to typical electrical meter movement 104 forms moving reflective surface acting as surface 64 of the other embodiments. To choose "set-point" of the meter-relay, the sensor head is moved inwards or outwards until null-point of the sensor head coincides with desired meter reading. This is the meter set-point and the electrical condition where an electrical amplifier connected in a differential mode to the light detectors (not shown) which receive reflected light transmitted by guides 28 and 30 will reverse output polarity to activate a relay of any suitable type (not shown).

Figure 15:
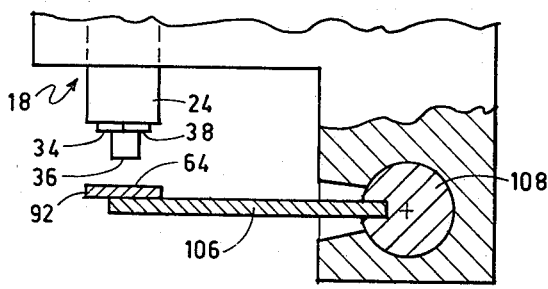
FIG. 15 shows the system of the invention as applied to sensing the rotational movement of a shaft.

FIG. 15 shows the device employed as a rotational limiter with a reflective body 92 having reflective surface 64, mounted on a radius by arm 106 and at right angles to axis of shaft 108, the sensor head can be used for precise control of angular movement of the shaft.

Figure 16:
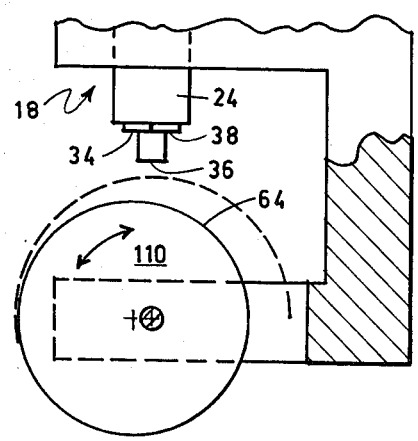
FIG. 16 is another fragmentary view showing the sensor used to monitor the rotation of an eccentric.

In FIG. 16 another form of rotational limiter is shown. A less precise but larger angular control can be secured if the shaft has an attached cam or eccentric 110. The device operates on the same principle as the meter relay of FIG. 12. This configuration could also be used for ignition timing when the number of cam-lobes equal the number of cylinders. Timing would be adjustable by rotating the collar 42. This would be simple with microprocessor controlled spark advance as well as vacuum controlled spark advance. This configuration could also be used for shaft revolutions counting and flow valve position indicator in the petroleum industry.

Figure 7:
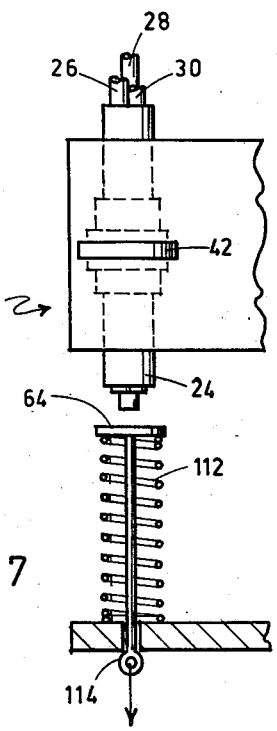
FIG. 7 is a front view, partly in section, showing the use of the proximity gauge as a force detector.

FIG. 7 shows the device as a force sensor. Using standard masses, a spring 112 is compressed (or stretched or bent) while recording each collar (micrometer) setting for each corresponding force value nullpoint. This can be done either manually or electronically with an automatic servo system. From this caibration curve unknown forces applied to the spring through rod 114 can then be measured and read out.

Figure 11:
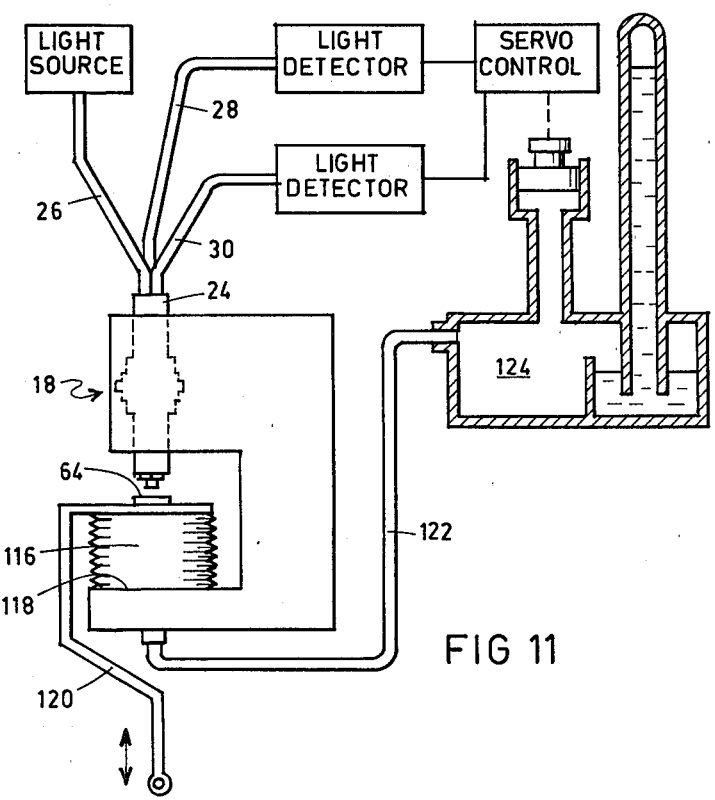
FIG. 11 is a diagrammatic representation of a fluid pressure control system employing a bellows in conjunction with the novel sensor.

In FIG. 11 another force sensor is shown. Bellows 116 is supported on platform 118. A compressive force is applied to the bellows through arm 120 thus increasing the pressure in line 122 and chamber 124 at the same time changing the relative intensities of reflected light. It should be noted that this sensor could easily be changed to an extremely accurate force sensor by introducing a yoke across the bellows, i.e., make arm 120 so that it can be attached for applying force axially to the bellows. The sensor would be nulled at atmospheric pressure and then the automatic pressure system of medical monitor (disclosed and described in detail in the incorporated application) would adjust the internal pressure of the resilient bellows so that the sensor would return to null while a force was being applied to the yoke. The restoring pressure required would now be a measure of force applied.

Figure 8:
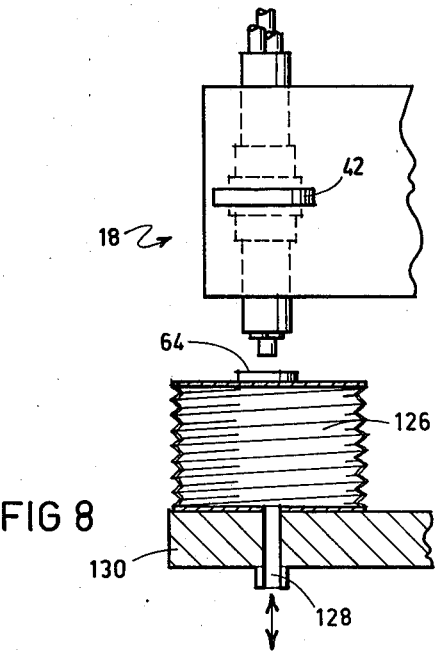
FIG. 8 is a similar view showing the sensor used to measure pressure in a fluid system.

A pressure sensor is shown in FIG. 8. While recording the position of the collar 42 (micrometer), a graded series of pressures is introduced into the bellows or diaphragm chamber 126 through duct 128. The bellows is supported on platform 130. With these pressures versus sensor position at null-point readings a calibration curve can be prepared such that unknown pressures can be measured accurately without errors due to friction and/or backlash in linkages. No explosion hazard exists in presence of organic vapors.

Figure 9:
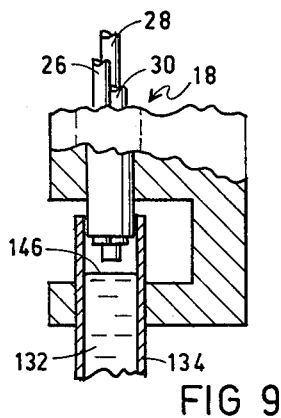
FIG. 9 is a fragmentary view, partly in vertical section, showing the sensor utilized as a liquid level indicator.
Figure 10:
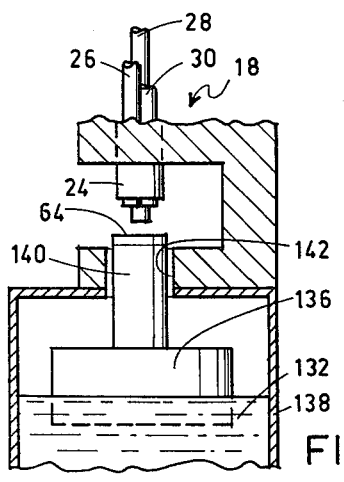
FIG. 10 is a view similar to FIG. 9, illustrating an alternative embodiment.

FIGS. 9 and 10 show liquid level sensors. In the embodiment of FIG. 9, the fluid 132 could be any reflective fluid. Examples are mercury at room temperature and molten lead, tin or aluminum at elevated temperatures. With the selection of quartz fiber optics and using ultra-violet light, the system could be made to function with other red hot metals or materials. With the appropriate wave-length light source organic fluids would also be highly reflective and their levels detected. The fluid 132 enters duct 134. The sensor is arranged to face the liquid surface 146.

Where for some reason direct access cannot be had to the liquid surface or the liquid is non-reflective in nature, the arrangement of FIG. 10 may be used. A float 136 is placed on the surface of the liquid 132 in container 138. A projection 140 on the flat extends upwardly through opening 142 and is provided with a reflective surface 64 which reflects light back to the sensor head as in the other embodiments. The sensor head may be located either inside or outside the tank which contains the liquid whose level is to be sensed.

In the various embodiments of the invention, the adjusting collar 42 (FIG. 1) or sleeve 74 (FIG. 1A) may be rotated manually or automatically by, for example, a reversible electric motor. By using a "stepper" motor or other electrical pulse output system, the sensor becomes suitable for use in digitally controlled systems using computers and microprocessors. The collar may be gear driven by a motor or in a better design, the collar itself is the armature of a hollow shaft permanent-magnet stepper-motor.

The differential three guide (three path) optical sensor of the invention is inherently less affected by stray or ambient light because only differences in light intensities are measured by paired photocells and, at the null point, almost exactly equal light intensities will reach each photodetector. The stray and/or ambient light is picked up almost equally by both output guides and is, therefore, cancelled out at the two photodetectors where only difference measurements are being made. The three guide assembly can also be made even more drift-free by source light chopping, but chopping leads to system complexity in either two guide or three guide systems, however.

Figure 13:
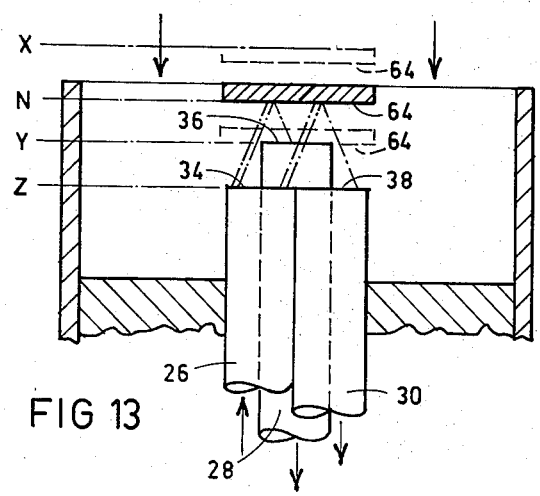
FIG. 13 is a fragmentary section of the light reflecting part of the sensor to illustrate the principle of operation.

The three guide assembly of the invention can be made even more resistant to ambient light by a shroud and special configurations of the fiber optics. Referring to FIGS. 1 and 1A, the outer cylindrical shroud 62 encloses the guide assembly and protrudes past face 36, but not out as far as the null plane N (FIG. 13). For use in a dirty environment the cavity thus formed could be filled with a clear plastic (the outer surface of which is flush with the outer end of the shroud) treated for low reflectance.

Where space is not a problem, multiple three guide sets could be bundled together and enclosed in a single shroud to minimize the effect of several individual ambient light sources. The light detector ends of each appropriate fiber type (26, 28 or 30) would, of course, lead to its corresponding light source or light detector. As an alternative multiple guide configuration multiple guides 28, 30 could form concentric circles around multiple guides 26. Multiple faces 36 would always protrude out past multiple faces 34 and 38 which would be even with each other. The selection of faces 36 or 30 to be the outer concentric circle (located just inside the cylindrical shroud) would be determined by a combination of the reflective characteristics of the reflective surface and the geometric location of the ambient light sources. The configuration with the least ambient light response would be chosen.

These novel sensor heads will function in the presence of high radiation levels and are therefore suited to position sensing in environments of high temperature, high radio frequency fields, high atomic radiation fields and intense magnetic fields, since the electronics themselves can be mounted very remotely (and safely) from these fields. There is also no ignition hazard to inflammable vapors by the sensor head.

For these reasons, the various designs would be of particular value for oil refineries and the nuclear power industry. Hence, the uses for the novel sensor are too numerous to mention and the embodiments illustrated and described are intended to be by way of example and not by way of limitation.

I claim:

1. A sensor for use in apparatus capable of translating the relative intensity of transmitted reflected light into signals indicative of the distance between the sensor and the reflective surface of a body which comprises means for directing light at said surface from a point source;

a pair of output light guides arranged with their light receiving ends facing said surface to receive and transmit the light reflected by said surface;

the light receiving end of one of said guides, when said sensor is in operative position, being closer to said surface than the other;

whereby the intensities of reflected light received and transmitted by said guides will be equal so as to indicate a null when said body is located a predetermined distance from said light receiving ends and will vary differentially as a function of change of distance between said body and said ends.

2. The combination of claim 1 wherein said means for directing light comprises an input light guide.

3. The combination of claim 2 wherein said light guides are mounted side by side in a housing and means are provided for adjusting the distance between at least the light receiving end of one of said pair of guides and said reflective surface.

4. The combination of claim 3 wherein said adjusting means is arranged to shift said housing and light guides in unison toward and away from said surface.

5. The combination of claim 3 wherein said adjusting means is arranged to shift toward and away from said surface only the one of said pair of output guides whose end, when the sensor is in operative position, is closer to said surface than the other.

6. The sensor of claim 1, wherein said sensor is adapted for sensing the position of a reflective body relative to the sensor by comparing the intensities of reflected light from the body,
the light receiving ends of said pair of guides being so disposed and arranged with respect to said reflective body that, when said body is close to said ends, a greater intensity of light from the input guide will be reflected by the surface of said body to one of said output guides, that, when said body is remote from said ends, a greater intensity of said light will be reflected by the surface of said body to the other of said output guides and, that, when said body is in a null position between said close and remote positions, the intensities of light reflected to said guides will be equal, whereby the intensities of reflected light transmitted by said output guides will vary differentially as a function of change of distance between said body and said ends in either direction from said null position.

7. The combination of claim 6 including means for detecting the intensities of reflected light transmitted by said output guides.

8. The combination of claim 7 including means responsive to said detecting means and actuated by a differential variation in said intensities for restoring the body to null position.

9. The combination of claim 7 wherein said body is a reflective liquid including means for holding said liquid with its surface opposite the ends of said guides whereby the level of said liquid may be sensed.

10. The combination of claim 7 wherein said body comprises a float having a reflective surface and floating on a liquid and means for holding said liquid and float with the reflective surface of the latter opposite the ends of said guides whereby the level of the liquid may be sensed.

11. The combination of claim 7 wherein said body comprises a reflector carried by a moving object which moves to at least one specified limiting position, whereby the differential variation of the intensities of reflected light is a function of deviation from said specified limiting position and wherein said sensor is mounted with the light receiving ends of said guides at said null position when said reflector is at said limiting position.

12. The combination of claim 7 wherein said body comprises reflecting means carried by a moving body which moves to at least one specified limiting position, said sensor being located with respect to said limiting position such that its light receiving guide ends will receive equal intensities of reflected light from said reflecting means only when said body occupies its said specified position whereby differential variation of the intensities of the reflected light is a function of the degree of deviation of said body from specification.

13. The combination of claim 7 wherein said moving body has more than one limiting position and a sensor is mounted to monitor each such position.

14. The combination of claim 12 or claim 13 wherein said body is subjected to reciprocating movement.

15. The combination of claim 12 wherein said body is subjected to rotational movement.

16. The combination of claim 7 wherein said reflective body comprises a portion of an indicator which moves toward and away from said light receiving ends with change of the conditions indicated by it and means for adjusting the light receiving end of at least one of said light receiving guides toward and away from the body to establish said null position at a predetermined reading of said indicator whereby a signal may be generated each time said indicator reaches said null position.

17. The sensor of claim 6, wherein said sensor is adapted for measuring the force applied to a resiliently deformable body, said sensor further comprising
means for detecting the intensities of reflected light transmitted by said output guides; and
means for applying a force to compress said body so that the distance between said reflecting means and said light receiving ends will vary proportionally, whereby said device may be calibrated to a series of nulls for corresponding force values.

18. The combination of claim 17 wherein said deformable body comprises a spring.

19. The combination of claim 17 wherein said deformable body comprises a bellows.

20. The sensor of claim 6, wherein said sensor is adapted for measuring force, said sensor further comprising
a bellows;
means for applying an unknown force to compress said bellows;
reflecting means on a movable surface of said bellows;
means for detecting and comparing the intensities of light transmitted by said output guides and generating a differential signal when said intensities are unequal;
a fluid pressure generating system responsive to said differential signal and in communication with said bellows for increasing the pressure therein until said transmitted light intensities are equalized, whereby said increased pressure is a measure of the force applied to said bellows.

21. The sensor of claim 1, wherein said sensor is adapted for gauging thickness, said sensor further comprising means for positioning the reflective surface of a body whose thickness is to be sensed in a predetermined location;
whereby the intensities of reflected light received and transmitted by said guides will be equal so as to indicate a null when said body is located a predetermined distance from said light receiving ends and will vary differentially as a function of change of distance between said body and said ends; and
means for detecting the intensities of said reflected light and translating the same into signals proportional to the thickness of the body thereby to detect departures from a specified thickness.

22. The combination of claim 21 including means responsive to said signals for adjusting the thickness of the body for restoring the body to its specified thickness and correspondingly restoring the distance between said surface and said guide ends to the predetermined null.

23. The combination of claim 22 wherein said body is a travelling sheet.

24. The combination of claim 21 wherein said light guides are bundled together in a housing mounted in a bracket so as to face said reflective surface, together with means for adjusting at least one of said light receiving ends toward and away from said surface for purposes of establishing said null position.

25. The combination of claim 24 wherein said adjusting means is arranged to move said housing bodily toward and away from said surface to establish said null position.

26. The combination of claim 24 wherein said adjusting means is arranged to shift longitudinally the one of said light receiving guides whose receiving end is closer to said surface.

27. The sensor of claim 1, wherein said sensor is adapted for sensing fluid pressure, said sensor further comprising
 a bellows in communication with said fluid, said bellows having reflecting means on a movable surface;
 means for directing light at said reflecting means from a point source; and
 light detecting means coupled to the outputs of said light guides;
 whereby the intensities of reflected light received and transmitted by said guides will be equal at a predetermined null position of said reflecting means with respect to said light receiving ends and will vary differentially as a function of change of distance between said ends and said reflecting means thereby permitting calibration of said sensor to a series of nulls for corresponding pressures.

* * * * *